United States Patent [19]

Duff et al.

[11] Patent Number: 4,905,706

[45] Date of Patent: Mar. 6, 1990

[54] METHOD AND APPARATUS FOR DETECTION OF HEART DISEASE

[75] Inventors: Bob M. Duff, San Antonio, Tex.;
Cynthia S. Gibson, Ft. Meade, Md.;
Dean C. Winter; H. Herbert Peel,
both of San Antonio, Tex.

[73] Assignee: Nippon Colin Co., Ltd., Komaki, Japan

[21] Appl. No.: 183,830

[22] Filed: Apr. 20, 1988

[51] Int. Cl.⁴ .................................................. A61B 5/04
[52] U.S. Cl. ...................................... 128/701; 128/700; 128/695
[58] Field of Search ................. 128/695, 696, 700, 701

[56] References Cited

U.S. PATENT DOCUMENTS

| | | | |
|---|---|---|---|
| 3,048,166 | 8/1962 | Rodbard | 128/2.06 |
| 3,052,756 | 9/1962 | Seven et al. | 179/1 |
| 3,280,817 | 10/1966 | Jorgensen et al. | 128/2.05 |
| 3,762,397 | 10/1973 | Cage | 128/2.05 |
| 4,450,838 | 5/1984 | Miodownik | 128/696 |
| 4,549,552 | 10/1985 | Groch et al. | 128/700 |
| 4,586,514 | 5/1986 | Schlager et al. | 128/700 |
| 4,628,939 | 12/1986 | Little et al. | 128/696 |

Primary Examiner—Francis Jaworski
Assistant Examiner—George Manuel
Attorney, Agent, or Firm—Gunn, Lee & Miller

[57] ABSTRACT

A method and apparatus for detection of coronary artery disease. The apparatus records and analyzes that portion of the phonocardiogram lying between about 100 to 600 Hz. An electrocardiogram is also recorded and examined in order to pinpoint the diastolic window of PCG data. This window of data is subject to autocorrelation analysis and spectral analysis, resulting in a partial correlation coefficient index and a power density index. A linear combination of these two indices results in a Cardiac Screening Index which is indicative of the presence or absence of coronary artery disease.

18 Claims, 3 Drawing Sheets

METHOD AN APPARATUS FOR DETECTION OF HEART DISEASE

BACKGROUND OF THE INVENTION

1. Field of the Invention

The present invention generally relates to techniques for detection of heart disease, and more particularly to a technique which reveals disorders of the coronary arteries.

2. Description of the Prior Art

Every year, more than 550,000 people die of heart attacks in the United States alone. In fact, heart disease is the number one killer of persons living in the U.S. Heart attacks are usually brought on by the accumulation of fat and other substances within the coronary arteries, those vessels which supply the heart itself with oxygen and nutrient rich blood.

Research scientists are getting closer to the secret of preventing heart attacks. The most important aspect of prevention is detecting the presence of arteriosclerosis before it advances to a critical stage. There are many techniques currently in use for monitoring various cardiac parameters. These include ballistocardiography, electrical impedance measurements, ultrasonics, electrocardiography, and vibrocardiography. These techniques, however, are invasive and require complex, expensive equipment.

Several patents have issued which deal with cardiac screening. For example, U.S. Pat. No. 3,280,817 issued to Jorgensen et al, discloses a method of screening which measures electrical heart activity; however, the effectiveness of this technique depends in large part on the definition of successive function time phases which is extremely subjective. In U.S. Pat. No. 3,048,166 issued to S. Rodbard, another apparatus and method is set forth which records low intensity, high frequency heart sounds; the recording must be played back at a slower speed for enhanced resolution. Also, U.S. Pat. No. 3,762,397 issued to J. Cage describes a similar system. This invention relates only to obtaining a clear trace of the heart sound, erasing any background noise. Finally, U.S. Pat. No. 3,052,756 issued to Seven et al. claims a phonocardiography apparatus which simply records abnormally high frequencies in the electrical undulations of the heart. However, at the present time there are few means for reliable interpretation of the results of these procedures.

It would therefore be desirable and advantageous to devise a simple, safe, and noninvasive method and apparatus for identifying coronary artery disease. The benefit of such a device would be greatly enhanced if it could be used by technicians or other non-medical personnel in screening large groups of people, without the need for a special clinic or hospital facilities. The device and method for detection of coronary artery disease which is the basis of this invention utilizes characteristic sounds produced by the heart.

SUMMARY OF THE INVENTION

Accordingly, the primary object of the present invention is to provide a method and apparatus for detecting cardiovascular disease.

Another object of the invention is to provide such a method and apparatus which does not require invasion of the body by instruments or by acoustic waves or electromagnetic radiation.

Still another object of the invention is to provide a simple method and apparatus by which non-medical personnel may screen patients for cardiovascular disease without the supervision of professional physicians.

The foregoing objects are achieved in a device and method for detection of coronary artery disease comprising a phonocardiogram coupled to a digitizer and processor which analyzes the acoustic energy of the heart in the frequency range of 100 to 600 Hertz. This energy is compared to certain statistical characteristics of the waveform, yielding a final screening index indicative of heart disease.

BRIEF DESCRIPTION OF THE DRAWINGS

The novel features believed characteristic of the invention are set forth in the appended claims. The invention itself, however, as well as a preferred mode of use, further objects and advantages thereof, will best be understood by reference to the following detailed description of illustrative embodiments when read in conjunction with the accompanying drawings, wherein:

DESCRIPTION OF THE PREFERRED EMBODIMENTS

It is well known that electrocardiogram (ECG) signals resulting from the electrical activity of the cardiac muscle are extremely valuable diagnostic indicators when viewed by an experienced cardiologist. Certain abnormalities in these signals can be indicative of different types of heart disorders. It has recently been discovered, however, that an alteration in the geometry or mechanical properties of a coronary artery will affect the vibrations and sound produced by the beating heart. The present invention consist of a method and apparatus for extracting information from acoustic heart signals and thereby identifying the existence of coronary artery disease.

Figure 1:
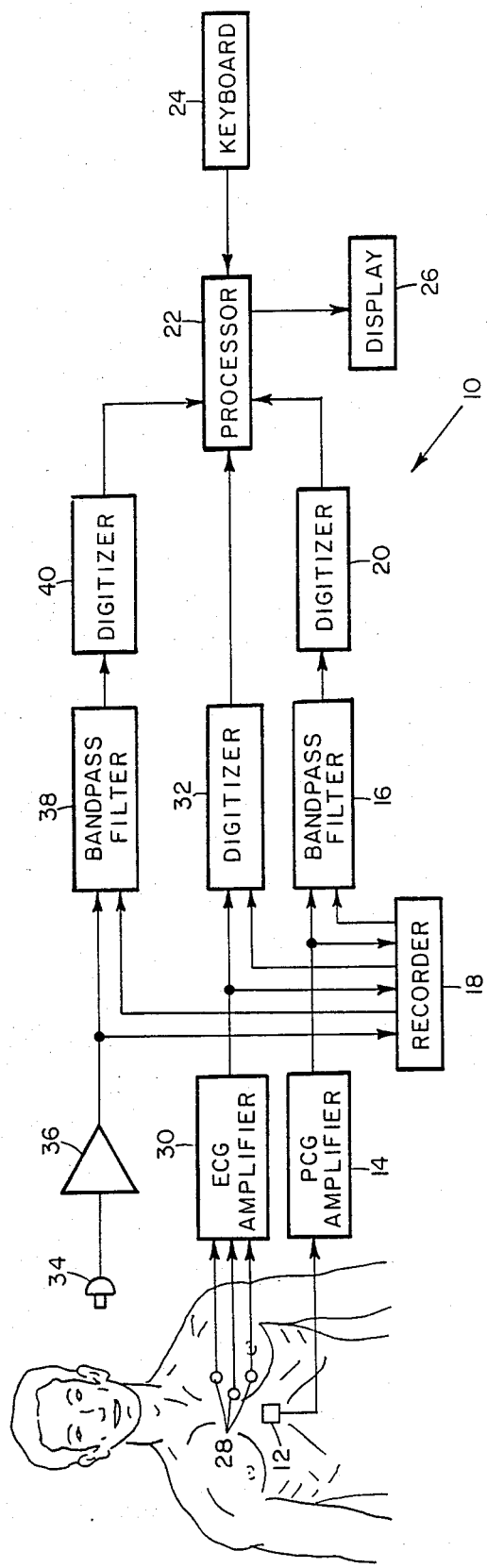
FIG. 1 is a block diagram showing the general components of the phonocardiogram monitoring system.

With reference not to the figures, and in particular with reference to FIG. 1, there is depicted a block diagram showing the general arrangement of phonocardiogram (PCG) monitor 10. A PCG microphone 12 is placed on the chest of the subject. PCG microphones are known in the art, and generally have piezoelectric crystals which pick up internal acoustical activity. The inventors prefer using a PCG microphone having transducers with a 0.01 microfarad capacitance per element. The microphone output is passed through an amplifier 14 and bandpass filter 16. The important information utilized by this device is contained in heart sounds whose frequency content lies between about 100 Hz and 600 Hz. The bandpass filter 16 therefore passes only frequencies within this range, removing the large amount of energy contained in the major heart sounds at frequencies less than 100 Hz, and attenuating any noise having frequencies above 600 Hz. It should be understood that these frequency limits are only approximate and may be varied somewhat.

The raw PCG signal is also passed to a recorder 18 for later playback and analysis. Recorder 18 is a conventional magnetic tape recorder, such as that manufactured by Racal of Irvine, Calif., under the trade name STOREHORSE. The conditioned PCG signal from bandpass filter 16 is output to a digitizer 20 and processor 22. Processor 22 is a conventional microprocessor having read only memory (ROM) in which certain instructions are stored, and random access memory (RAM) for storing temporary variables used in data analysis. Processor 22 has connected thereto a keyboard 24 for controlling processing parameters, and a display 26 (simply a cathode ray tube) which allows the operator to review the PCG and ECG scans, as well as examine the results of the screening process.

In addition to PCG microphone 12, a set of ECG electrodes 28 are also placed on the body. The signal from ECG electrodes 28 is routed to an ECG amplifier 30, and then to both recorder 18 and another digitizer 32. Finally, the digitized ECG signal is transmitted to processor 22, where it is used to correlate the PCG signal with specific heart sounds.

In the preferred embodiment, the effect of ambient noise within the room in which the measurements are taken is removed by means of acoustic microphone 34. Acoustic microphone 34 is mounted near the subject but not in contact with the body. The signal from acoustic microphone 34 is passed through an amplifier 36, another bandpass filter 38 similar to filter 16, and then digitized by another digitizer 40 which transmits the digital signal to processor 22. Processor 22 then subtracts out the ambient signal from the PCG signal.

In an alternative embodiment (not shown), PCG amplifier 14 is a differential amplifier having inputs from both PCG microphone 12 and acoustic microphone 34. In this manner, the differential amplifier simply cancels ambient noise from the acoustic heart signal before further signal conditioning. In this regard, it should be noted that acoustic microphone 34 is not essential to the practice of the present invention, but it considered desirable.

An important part of this invention lies in the method whereby evidence of coronary artery disease (CAD) is extracted from the heart sound data. It is anticipated that the data analysis functions described here will be performed by processor 22, but alternative embodiments may perform certain functions by analog circuits placed before digitizer 20. Specifically, the total power computation discussed below could be accomplished by a bandpass integrator (not shown).

Figure 2:
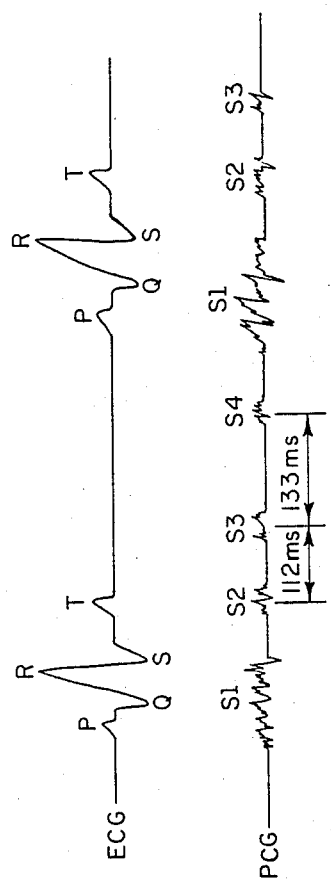
FIG. 2 consists of two side-by-side plots showing electrical activity of the heart and the corresponding acoustic activity.

In order to understand the present invention, it is necessary to explain the nature of the ECG and PCG signals. With reference now to FIG. 2, representative ECG and PCG signals are shown. As is familiar to those skilled in the art, a typical ECG signal consists of a P-Q-R-S-T event. This classical wave form includes a P-wave of positive polarity, a Q-R-S complex consisting of a negative Q-wave, a positive R-wave, and a negative S-wave, and a T wave that is separated from the Q-R-s complex by a so-called S-T segment. The P-wave corresponds to the initial impulse that controls the commencement of the heartbeat. The Q-R-S complex represents the stimulus which triggers the ventricular contraction which produces the actual cardiac pumping action. The R-wave is particularly important as it always appears as a sharp spike, and therefore is fairly easily identified. The T-wave relates to the repolarization of the ventricles. There may be several additional waves present in a normal ECG signal but since they have no relevance to the present invention, this description is adequate for our purposes.

FIG. 2 also shows a typical PCG signal, representing acoustical activity in and around the heart. A first heart sound S1 commences about the same time as the P-wave appears, and continues throughout the Q-R-S complex. The first heart sound is caused by the closure of the atrioventricular valves (the tricuspid valve and the bicuspid or mitral valve) and the contraction of the ventricles. After a brief interval, a second rapid heart sound S2 appears, caused by the closing of the aortic and pulmonary valves. Diastolic blood flow begins after the second heart sound, resulting in a third heart sound S3. It is presently believed that the third heart sound is caused by the oscillation of blood back and forth between the walls of the ventricles initiated by inrushing blood from the atria. A fourth heart sound S4, also known as the atrial heart sound, occurs when the atria contract, which initiates vibrations in the ventricles similar to the third heart sound.

Thus, the four heart sounds result from valve closure (S1 and S2) oscillation of blood between the walls of the ventricle (S3) or contraction of the atria (S4). However, PCG activity also exists between these heart sounds. It is the "non-heart sound" PCG analysis which is the subject of this invention (the "flat" regions of the PCG signal illustrated in FIG. 2).

In the past, scientists have found correlations between phonocardiograms and heart disease, but this has been fairly limited to graphic examination of the PCG only, and is further only useful in detecting valvular lesions. The inventors of the present device, however, have found that a statistical analysis of that portion of the PCG lying roughly between the third and fourth heart sounds is very useful in detecting coronary artery disease. That is, the present device is designed to analyze a portion of the PCG which occurs after the second heart sounds and which excludes the third and forth heart sounds, but includes acoustical activity emanating from the arteries. Specifically, the present device analyzes the diastolic window beginning about 112 milliseconds after the peak of the second heart sound and lasting about 133 milliseconds. This period is referred to herein as the cardiac screening window.

The method presented in this invention involves two parameters of heart sound, the first relating to the partial correlation coefficients of the cardiac screening window, and the second relating to the total power density in this window, both factors being limited to the bandwidth of approximately 100 to 600 Hz. This bandwidth is selected to eliminate the large amount of energy contained in the major heart sounds at frequencies less than 100 Hz., and also noise having frequencies above 600 Hz.

Partial correlation coefficients, also referred to as reflection coefficients, are a measure of the strength of association between a dependent variable (here, the PCG signal) and an independent variable (here, time). Numerical techniques for computing partial correlation coefficients are well known to those skilled in the art. A good discussion of these techniques is contained in "Programs for Digital Signal Processing," published by the IEEE Press in 1979 (Chapter 4). The present invention, however, is especially concerned with the third and fourth partial correlation coefficients. Specifically, it has been empirically found that the difference between these two coefficients is somewhat indicative of coronary artery disease. This difference (between the third and fourth partial correlation coefficients) is referred to hereafter as the PARCOR Index. As further discussed below, one of the functions of processor 22 is to compute the PARCOR Index for a series of heartbeats. The inventors have found the software package entitled "Digital Data Processing," distributed by the IEEE, to be useful in this regard.

The second parameter of concern, the power density in the cardiac screening window, is determined by spectral analysis, also well known in the art. The power density spectra are normalized to the average peak to peak amplitude of the first and second heart sounds (explained further below). This parameter is referred to herein as the Power Index. The IEEE software package referred to above is also capable of performing the necessary spectral analysis. As with the PARCOR Index, the Power Index has been found to aid in the detection of coronary heart disease; however, it has been found that significantly better sensitivity and specificity are obtained by using a linear combination of the PARCOR and Power Indices. This combination, designated the Cardiac Screening Index, is discussed in relation to FIG. 3.

Operation

Figure 3:
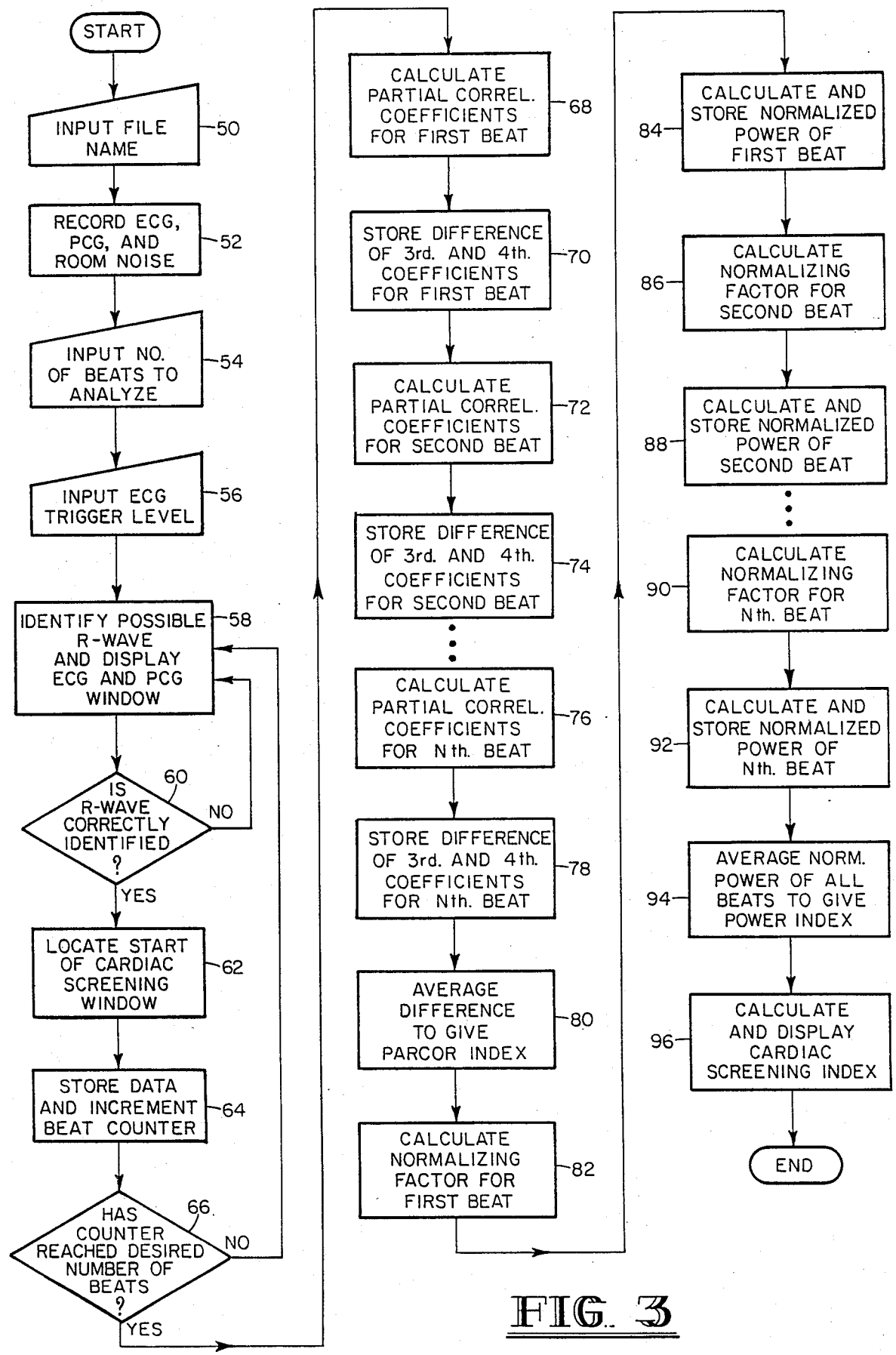
FIG. 3 is a flow chart of the analysis undertaken by the analyzer element of the invention.

The operation of the device of the present invention is best understood with reference to FIG. 3. FIG. 3 is a chart of the logic flow of the program residing in processor 22. After the patient has been fitted with ECG electrodes 28 and PCG microphone 12, the operator begins the session by entering a file name for the data to be subsequently analyzed (50). The recorder 18 is then turned on, and the data (ECG, PCG, and room noise) is taken (52). Because of the significant problems caused by room noise, care should be taken to avoid data acquisition in an extremely noisy environment. Typically, only about forty seconds of data need be taken. This depends on the number of heartbeats to be analyzed (discussed below); a forty second sample usually yields about 30-50 heartbeats. The information is immediately recorded for later playback, but may also be analyzed immediately as it is stored (in digitized form) in the RAM of processor 22.

After the input data has been taken, the operator begins processing of the data by first selecting the number of heartbeats to analyze (54). The inventors have found that a minimum of nine heartbeats is desirable to insure accurate results. After entering this number, the operator next selects the ECG trigger level for identifying the R-wave of any given heartbeat (56). It is necessary to identify the R-wave in order to isolate the cardiac screening window of the PCG. Actually, this could be done by triggering off the first heart sound S1, but the inventors have found that the first heart sound is sometimes obscured, and so the ECG trace provides a more reliable means of discriminating between heartbeats. It should be understood, however, that the present invention could be practiced entirely without the ECG provided the operator was especially diligent in examining the phonocardiogram.

The ECG trigger level (56) is used in the peak detection routine stored in processor 22. If the R-wave peaks are significantly higher than the T-wave peaks, then a pure peak detection routine is used. If not, a slope detection routine is first used to find the rising edge of the R-wave and then the peak is found using the peak detector routine. For a detailed discussion of R-wave detection, attention is directed to U.S. Pat. No. 3,858,034, which hereby incorporated by reference.

After the operator has entered all preliminary operating parameters, processor 22 begins analysis of the data by identifying the R-wave of the first heartbeat, and displaying a one second window of ECG and PCG data beginning at the R-wave (58). The operator then determines if the R-wave peak has been correctly identified (60). If not, processor 22 looks for a new peak. If so, the operator locates the starting point of the cardiac screening window (62), and the data for this window is put in temporary storage (64). Also, the counter which keeps track of the number of acceptable beats is incremented. This continues until the number of samples reaches the number previously input by the operator in step 54. The graphic inspection of the PCG and ECG data by the operator is not entirely necessary as R-wave peak detection and the cardiac window selection may be performed automatically, but, as noted above, due to possible aberrations in the signals, manual inspection is deemed desirable.

After a sufficient number of good PCG samples have been selected (66), processor 22 begins calculation of the partial correlation coefficients. First, the partial correlation coefficients for the first beat are determined (68), and the difference between the third and fourth coefficients is put in temporary storage (70). This is repeated for the second beat (72, 74), and so on until the Nth beat (76, 78). When these values have been determined for all beats, they are then averaged to give the PARCOR Index (80).

The next series of steps relates to the Power Index. First, the normalizing factor for determining the power density is calculated for the first heart beat (82). This is simply an average of the peak-to-peak amplitudes of the first and second heart sounds. In other words, the amplitudal variation of the first heart sound is added to the amplitudal variation of the second heart sound, and this sum is divided by two. The result is then used in a fast Fourier transform routine to yield the normalized power density of the first beat (84). This is repeated for the second beat (86, 88), and so on until the Nth beat (90, 92). When the normalized power for all beats has been determined, these values are averaged to yield the Power Index (94).

Figure 4A:
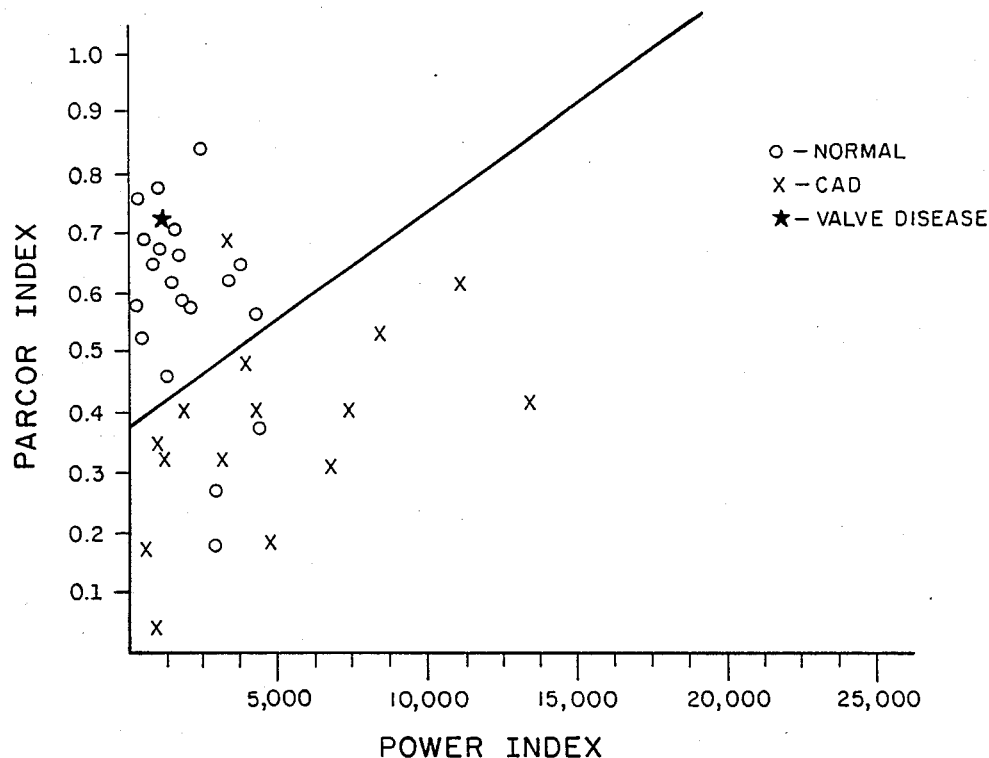
FIGS. 4A and 4B depict Cardiac Screening Indices based on empirical observations.
Figure 4B:
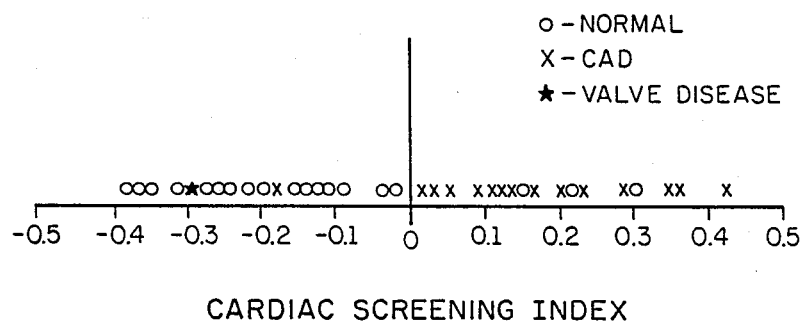

The final step in the method of the present invention is to combine the PARCOR and Power Indices to give the Cardiac Screening Index, which is then displayed to the operator (96). The Cardiac Screening Index may best be understood with reference to FIGS. 4A and 4B. FIG. 4A is a plot of the Power Index versus the PARCOR Index for an actual test group consisting of patients at Humana Hospital and Southwest Research Institute in San Antonio, Tex. An "X" represents individuals with known coronary artery disease, while a "O" represent individuals free from such disease. The star symbol represents an individual who had a valve disease, but not CAD.

As can easily be seen, there is a distinct pattern to the location of the "X" individuals compared to the "O" individuals. First of all, it should be noted that, as previously mentioned, either one of the Power or PARCOR Indices may be useful in detecting CAD. Specifically, it can be seen that a relatively low value of PARCOR Index indicates positive results for testing, while a high PARCOR Index indicates negative results. Similarly, there is a qualitative relationship between the Power Index and the presence of CAD. Plotting both of these values, however, results in a significantly better interpretation of the data. Based on these empirical values, the inventors have generated a linear combination of the Power and PARCOR Indices which results in the Cardiac Screening Index. Based on the equation for the line drawn in FIG. 4 between the "X" and "O" groupings, the Cardiac Screening Index (CSI) is given by the following equation:

$$CSI = [0.0000358 \times (\text{Power Index})] - (\text{PARCOR Index}) + 0.375.$$

By using this equation, the operator may obtain an immediate conclusion on CAD merely by examining the sign (positive or negative) of the Cardiac Screening Index. This is reflected in FIG. 4B, which is a plot of the CSI for the same data points shown in FIG. 4A. These empirical results show that a positive CSI corresponds to the presence of coronary artery disease, while a negative CSI corresponds to the lack of such disease.

The inventors caution against rigid interpretation of the results of this screening method inasmuch as the equation given above for determining the CSI may be affected by other variables, such as the signal-to-noise ratio in the phonocardiogram. However, it can be seen from FIGS. 4A and 4B that the positive test results were accurate 87.5% of the time, and negative test results were accurate 85% of the time.

Although the invention has been described with reference to specific embodiments, this description is not meant to be construed in a limiting sense. Various modifications of the disclosed embodiment, as well as alternative embodiments of the invention will become apparent to persons skilled in the art upon reference to the description of the invention. It is therefore contemplated that the appended claims will cover such modifications that fall within the true scope of the invention.

I claim:

1. An apparatus for detecting heart disease from a cardiac acoustical signal consisting of a plurality of heartbeats, said apparatus comprising:
   means for converting the acoustical signal into an electrical signal;
   means for digitizing said electrical signal; and
   means for analyzing said digitized electrical signal, said analyzing means including:
      means for calculating an average difference between the third and fourth partial correlation coefficients of said plurality of heartbeats;
      means for determining the average power in said plurality of heartbeats; and
      means for correlating said average difference between said third and fourth partial correlation coefficients with said average power whereby the presence of coronary artery disease may be ascertained.

2. The apparatus of claim 1 wherein said analyzing means analyzes only said digitized electrical signal corresponding to said cardiac acoustical signal which lies approximately between the third and fourth heart sounds of each of said plurality of heartbeats.

3. The apparatus of claim 2 further comprising means for recording an electrocardiogram associated with said cardiac acoustical activity, said recording means operatively associated with said analyzing means for demarcating said cardiac acoustical activity by detecting the Q-R-S peaks in said electrocardiogram corresponding to each of said heartbeats, said analyzing means further capable of correlating said peaks with said third and fourth heart sounds.

4. The apparatus of claim 3 further comprising means for filtering said cardiac acoustical activity, said filtering means being operatively connected to said digitizing means, whereby only that portion of said cardiac acoustical activity lying within the frequency range of approximately 100 to 600 Hertz is analyzed.

5. The apparatus of claim 4 further comprising means for graphically displaying said electrocardiogram whereby an operator may visually detect said Q-R-S peaks used to demarcate said cardiac acoustical activity, said displaying means operatively associated with said analyzing means.

6. The apparatus of claim 5 further comprising keyboard means for selecting analysis parameters utilized by said analyzing means, said keyboard means operatively associated with said analyzing means.

7. The apparatus of claim 6 further comprising means for recording ambient acoustical noise, said ambient noise acoustical recording means being operatively connected to said analyzing means whereby said ambient acoustical noise may be cancelled out from said cardiac acoustical activity.

8. An apparatus for detecting heart disease comprising:
   a phonocardiogram microphone for detecting cardiac acoustical activity consisting of a plurality of heartbeats;
   electrodes for detecting an electrocardiogram associated with said cardiac acoustical activity;
   means for recording said cardiac acoustical activity and said electrocardiogram, said recording means being connected to said microphone and said electrodes;
   means for graphically displaying said electrocardiogram whereby Q-R-S peaks corresponding to said plurality of heartbeats may be displayed;
   means for correlating a given one of said Q-R-S peaks to a window of said cardiac acoustical activity, said window lying approximately between said third and fourth heart sounds;
   processor means for calculating an average difference between the third and fourth partial correlation coefficients associated with said plurality of heartbeats, for determining the average power in said plurality of heartbeats, and for correlating said average difference between said third and fourth partial correlation coefficients with said average power whereby the presence of coronary artery disease may be ascertained.

9. The apparatus of claim 8 further comprising means for filtering said cardiac acoustical activity, said filtering means being operatively connected to said processor means, whereby only that portion of said cardiac acoustical activity lying within the frequency range of approximately 100 to 600 Hertz is processed.

10. The apparatus of claim 8 further comprising means for digitizing said cardiac acoustical activity before processing by said processor means.

11. The apparatus of claim 8 further comprising:
    a PCG amplifier connected to said phonocardiogram microphone; and
    an ECG amplifier connected to said electrodes.

12. The apparatus of claim 8 further comprising an acoustic microphone connected to said processor means whereby ambient acoustical noise may be cancelled out from said cardiac acoustical activity.

13. An apparatus for detecting heart disease comprising:
- a phonocardiogram microphone for detecting cardiac acoustical activity consisting of plurality of heartbeats;
- electrodes for detecting an electrocardiogram associated with said cardiac acoustical activity;
- an acoustic microphone for cancelling out ambient acoustical noise from said cardiac acoustical activity;
- a PCG amplifier connected to said phonocardiogram microphone;
- an ECG amplifier connected to said electrodes;
- means for recording said cardiac acoustical activity and said electrocardiogram, said recording means being connected to said PCG and ECG amplifiers;
- a bandpass filter connected to said PCG amplifier, whereby only that portion of said cardiac acoustical activity lying within the frequency range of approximately 100 to 600 Hertz is passed;
- means for digitizing said cardiac acoustical activity and said electrocardiogram, said digitizing means being operatively connected to said bandpass filter and said ECG amplifier;
- means for graphically displaying said electrocardiogram whereby Q-R-S peaks corresponding to said plurality of heartbeats may be displayed;
- means for correlating a given one of said Q-R-S peaks to a window of said cardiac acoustical activity, said window lying approximately between said third and fourth heart sounds; and
- processor means connected to said digitizing means and said acoustic microphone for calculating an average difference between the third and fourth partial correlation coefficients associated with said plurality of heartbeats, for determining the average power in said plurality of heartbeats, and for correlating said average difference between said third and fourth partial correlation coefficients with said average power whereby the presence of coronary artery disease may be ascertained.

14. A method of detecting heart disease comprising the steps of:
- recording cardiac acoustical activity consisting of a plurality of heartbeats;
- filtering out that portion of said cardiac acoustical activity lying outside of the frequency range of approximately 100 to 600 Hertz;
- analyzing a plurality of windows of said filtered cardiac acoustical activity lying approximately between the third and fourth heart sounds of each of said plurality of heartbeats, said analyzing step including the stops of:
  - calculating an average difference between the third and fourth partial correlation coefficients associated with said windows, yielding a PARCOR Index;
  - determining the average normalized power in said plurality of heartbeats, yielding a Power Index; and
  - linearly combining said PARCOR and Power Indices to yield a Cardiac Screening Index, said Cardiac Screening Index being indicative of the presence of coronary artery disease.

15. The method of claim 14 further comprising the steps of:
- recording an electrocardiogram associated with said cardiac acoustical activity;
- detecting the Q-R-S peak for each of said plurality of heartbeats; and
- utilizing said Q-R-S peaks to demarcate said windows of said filtered cardiac acoustical activity.

16. The method of claim 14 further comprising the step of digitizing said cardiac acoustical activity before said analyzing step.

17. The method of claim 15 further comprising the step of first digitizing said cardiac acoustical activity and said electrocardiogram before said analyzing step.

18. The method of claim 17 further comprising the steps of:
- recording ambient acoustical noise;
- digitizing said ambient acoustical noise; and
- cancelling out said ambient acoustical noise from said cardiac acoustical activity before said analyzing step.

* * * * *